(12) United States Patent
Buck (10) Patent No.: US 6,231,840 B1
(45) Date of Patent: May 15, 2001

(54) COMPOSITIONS AND METHODS FOR THE TOPICAL TREATMENT OF NAIL FUNGI CONDITIONS

(76) Inventor: Carol J. Buck, 30 Brooks Bend, Princeton, NJ (US) 08540

( * ) Notice: Subject to any disclaimer, the term of this patent is extended or adjusted under 35 U.S.C. 154(b) by 0 days.

(21) Appl. No.: 09/081,256

(22) Filed: May 19, 1998

Related U.S. Application Data (63) Continuation-in-part of application No. 09/023,449, filed on Feb. 13, 1998.

(51) Int. Cl.[7] .............. A61K 6/00; A61K 7/00; A61K 7/04; A01N 25/34
(52) U.S. Cl. ................ 424/61; 424/61; 424/405
(58) Field of Search ............... 424/61, 401, 404, 424/405; 514/858, 859, 863, 887

(56) References Cited

U.S. PATENT DOCUMENTS

| | | | |
|---|---|---|---|
| 3,654,936 | * | 4/1972 | Wajaroff ................... 132/7 |
| 4,030,512 | * | 6/1977 | Papantoniou et al. ........... 132/7 |
| 4,363,815 | * | 12/1982 | Yu et al. .................. 424/274 |
| 4,424,820 | * | 1/1984 | Cannell et al. ............... 132/7 |
| 4,859,459 | * | 8/1989 | Greiche et al. ............... 424/71 |
| 5,091,171 | * | 2/1992 | Yu et al. .................. 424/642 |
| 5,635,168 | * | 6/1997 | Burns et al. ................ 424/70.4 |
| 5,661,170 | * | 8/1997 | Chodosh ................... 514/390 |

* cited by examiner

*Primary Examiner*—Thurman K. Page
*Assistant Examiner*—Sharon Howard
(74) *Attorney, Agent, or Firm*—Mathews, Collins, Shepherd & Gould, P.A.

(57) ABSTRACT

Compositions and methods for treating keratin-related conditions and disorders such as straightening and styling hair, treating nail fungal conditions such as onychomycosis, ingrown nails, and hyperkeratotic conditions of the epidermis such as psoriasis, acne, callouses, corns, verruca, particularly plantar warts, and surface lines and blemishes of aging skin by aiding the exfoliation of keratinocytes. The compositions comprise at least one alkanoic acid in aqueous solution.

12 Claims, 8 Drawing Sheets

HAIR OF CAUCASIAN SUBJECT WITH NATURALLY CURLY HAIR, PRE AND POST TREATMENT

BEFORE

AFTER

FIG. 1.
HAIR OF CAUCASIAN SUBJECT WITH NATURALLY CURLY HAIR, PRE AND POST TREATMENT

BEFORE

AFTER

FIG. 2.
RELAXING OF AFRICAN-AMERICAN HAIR AFTER ONE TREATMENT vs. CONTROL

CONTROL LOCKS

TREATED LOCKS

FIG. 3.

STRAIGHTENING OF VIRGIN AFRICAN AMERICAN HAIR AFTER 5 TREATMENTS

UNTREATED　　　　　　　　　AFTER 5 TREATMENTS

FIG. 4.

HAIR CURLING AGENT: IMMEDIATELY FOLLOWING INITIAL TREATMENT

RESIDUAL CURLING PROPERTIES - TWO WEEKS
POST INITIAL TREATMENT (SET DRY)

4 BRUSH STROKES

10 BRUSH STROKES

20 BRUSH STROKES

TREATMENT OF ONYCHOMYCOSIS AND HYPER KERATOSIS

PHOTOGRAPHS OF PATIENT'S GENERALIZED CALLOUS AND OM ON LARGE TOENAIL PRIOR TO AND AFTER TREATMENT AS DISCUSSED IN EXAMPLE 9.

FIG. 8.

COMPOSITIONS AND METHODS FOR THE TOPICAL TREATMENT OF NAIL FUNGI CONDITIONS

This application is a continuation-in-part of U.S. Ser. No. 09/023,449, filed Feb. 13, 1998.

FIELD OF THE INVENTION

This invention relates to compositions and methods for treating keratinous tissue for purposes of straightening hair, enhancing curl retention of hair, treating nail fungal conditions, including onychomycosis, ingrown nails, hyperkeratotic conditions, including psoriasis, acne and keratosis pilaris, callouses, corns, plantar wart, Dowling-Meara form of epidermolysis bullosa simplex, ichthyosiform dermatoses, and surface lines and blemishes of aging skin by exfoliation of keratinocytes.

BACKGROUND OF THE INVENTION

Hair Treatment

Human hair is a thermoset of cross-linked, α-helix protein, primarily keratin. Keratin is composed of a complex of polypeptide chains of high molecular weight. Protein sequencing analysis of whole hair fiber using acid hydrolysis has found traces of all the amino acids in human hair, but suggests that cystine, glutamic acid, serine, leucine, aspartic acid, arginine and threonine are among the amino acids of highest prevalence in hair.[1] The human hair shaft is comprised of three concentric layers identified as the cuticle, a thin, outer-most shell, the cortex, the main body of the hair, and the medulla, a thin, central core. The cuticle and cortex are responsible for the hair shaft's mechanical properties (in some hair the medulla is absent). The cuticle is composed of flattened, scale-like platelets of amphoras keratin. Its condition is responsible for the outward appearance of the hair, particularly feel and shine. The cortex forms and is composed of long keratinous spindle cells containing numerous macrofibrils of intermediate filament protein, held together by an intercellular matrix of beta-keratose. Each macrofibril contains 11 protofibrils in a helical structure. Each of the protofibrils is composed of three alpha-helices, the fundamental fibrous keratin.

[1] Gillespie and Inglis, *Total S-Carboxymethyl Keratin Extracted from Guinea Pig Hair by Standard Methods* (1965).

Alpha-helical keratin maintains its coil-shaped secondary structure by the use of hydrogen bonding between adjacent turns of the coil and by ionic bonding or salt bridges which pair the amine bases, lysine and arginine to the carboxylic acids, aspartic acid and glutamic acid. The method described herein changes the charge on the carboxylic acids within keratin causing both the loss of hydrogen bonding properties and the cleavage of the salt bridges. Secondary to these events is the disassociation of some of the disulfide bridges, or cystine bonds from the helix structure itself which are a principle force in the maintenance of natural curl. With the loss of hydrogen and ionic bonding, the keratin is partially denatured. The shaft becomes less sensitive to external moisture and more sensitive to heat-induced curling. With the partial loss of secondary and tertiary structure involving disulfide bridges, naturally curly hair loses its wavyness.

Those amino acids which are affected by the electron protonation of weak carboxylic acids (aq) resulting from the protonation of glutamic acid and aspartic acid are marked below by an asterisk.

The Amino Acid Composition of Hair Follicle Proteins (residues per 1000 amino acid residues)[2]

| Amino Acid | Residues |
|---|---|
| Cys | 160* |
| Asp | 52* |
| Thr | 59 |
| Ser | 97 |
| Glu | 127* |
| Pro | 52 |
| Cit | 0 |
| Gly | 50 |
| Ala | 54 |
| Met | 0 |
| Ile | 31 |
| Leu | 64 |
| Tyr | 30 |
| Phe | 43 |
| Lys | 24* |
| His | 12 |
| Arg | 71* |
| Isopeptide | Trace |

[2]Gillespie and Inglis, 1965, total S-carboxymethyl keratin extracted from guinea pig hair by standard methods.

Hair can be divided into four conformational categories: (i) straight, (ii) wavy, (iii) curly, and (iv) kinky. The amount of curl is directly associated with two factors: the alignment and shape of the follicle in the epidermis (the more angulated the follicle the more curly) and the shape of the shaft itself Straight hair resembles a rod with a circular diameter; wavy hair shafts are compressed into an oval diameter; curly shafts are further compressed into an elongated ellipse and kinky hair shafts are flatter still. Hair shaft configurations are as follows:

| Straight | Wavy | Curly | Kinky |
|---|---|---|---|

The elastic behavior of most hair types when wet is due to the hydrogen bonding that occurs between adjacent coils of keratin's secondary α-helix structure.[3] Hair becomes straighter when wet because hydrogen bonds—connecting the amino group of one amino acid and the oxygen of the third amino acid beyond it—are easily broken in water. The polypeptide chain can then be pulled out of its compact helical shape into a more extended form. As the hair dries the hydrogen bonds reform and the chains contract into their normal length. A similar, reversible breaking of hydrogen bonds occurs when hair is subject to tension or heat, as demonstrated by heat curlers, heat wands and heat combs. Keeton et al. describe the rubberband-like hydrogen bonds of α-helix keratin coils.[4]

[3] Knowlton, John, *Handbook of Cosmetic Science and Technology*, Justine-Avon Pty, South Africa. Excerpted from the chapter, The Structure of Hair, Cosmetic Science & Technology On-Line contents page.
[4] Keeton, W. T., Gould, J. L., *Biological Science*, 5th Ed., W.W. Norton, New York, 1993, p. 67.

To permanently alter the natural curl or straightness of human hair, a number of types of bonds must be cleaved, including salt bridges and disulfide bonds.[5] Disulfide bridges (cystine bridges) often serve to attach separate keratin strands or hold the strand within the surrounding matrix. Current permanent waving and straightening methods break disulfide bonds into free sulfhydryls and then re-establish new disulfide bonds in the desired configuration by reduction/oxidation of the hair shaft using various chemicals sequentially. This manipulation of sulfur (S) within cysteine is possible by alkalis, bisulfides and other chemicals because cystine's small, aliphatic side chains contain polar groups that ionize readily. Nevertheless, the process is harsh on the hair and potentially harmful to the skin.

[5] Menefee, E., Relation of keratin structure to its mechanical behavior, *Appl. Polymer Symposium*, 18, 809–821.

Disulfide bridges are most predominant in the outermost layer of the shaft's cuticle, the epicuticle, with progressively less found in the cuticle's sublayers, the exocuticle and endocuticle. The epicuticle also contains more disulfide bonds than does the matrix of the cortex.[6]

[6] The amount of cysteine and sulfur in tissue determines its hardness—tortoise shells, hooves, and horns are examples of the strength derived from cysteine bridges when up to one amino acid in four is cysteine. Keeton, W T, Gould, J. L., *Biological Science*, 5th Ed., WW Norton, New York, 1993., p. 67.

Current Methods of Permanent Hair Waving and Relaxing. New mechanical structure is imposed on hair shafts on a semi-permanent basis by the use of several types of chemicals capable of cleaving and reforming disulfide bonds in a two step process (reduction and oxidation) that results in the temporary denaturing of hair protein.[7] Several formulation improvements and additives have been developed in an effort to reduce the harshness of these chemicals and maintain pliable hair properties. Current methods, however, remain dangerous to the skin and eyes. Direct contact can result in second- and third-degree chemical burns or even hair loss.[8] None of the known methods are recommended if the scalp or skin is sensitive, scaly, scratched, sore or tender, and unsatisfactory, sometimes harmful results occur if the directions are not carefully followed.

[7] *Biochemistry* 2001: *Introductory Biochemistry*, Mount Allison University, Dr. A. Cockshutt (1997); *Protein Function: Folding of Structural proteins: Course Outline and Lecture Notes, Winter Term* 1997.
[8] *The A.M.A. Book of Skin and Hair Care*, Schoen, L A, Ed., American Medical Association, J.B. Lippincott Company, NY, 1976. p. 116.

During the permanent wave or straightening process, the hair is reshaped into waves with appliances or pulled straight by combing with lotions containing reducing agents. After 10 to 20 minutes, the free sulfhydryl groups are reoxidized and the hair conditioned and set with the desired conformity. While in a reduced state, the sulfhydryls within the matrix and protofibrils slide past each other as the protein is temporarily denatured. Once reoxidized, however, they form new cystine bridges and maintain this bond for a period of weeks or months.

Most permanent hair-waving and straightening products marketed today use one of five types of chemicals: (1) thioglycolate-based products, (2) sulfite-bisulfite products, (3) sodium hydroxide (alkali) products[9], (4) lithium hydroxide and (5) acetamide (formulated as a between-shampoos, aerosol styling aid). In (1)–(4), the chemical lotion is applied to clean, damp hair that has been set in curlers or pulled straight by combing action. After a carefully-measured period of time, the disulfide bonds are broken, the solution is rinsed off, and a second solution (often hydrogen peroxide or other oxidizing agent) is applied to neutralize the reaction. Thioglycolate wave creams and straighteners produce reversible changes in the chemical disulfide bonds of hair by generating free oxygen radicals for 10 to 20 minutes. Thioglycolate may induce breakage if the hair has been bleached, dyed, previously straightened or permed.[10] Concern about the teratogenicity of thioglycolate has recently caused the United States Department of Health and Human Services to post notice of a need to review their safety for human use.[11]

[9] *The AMA Book of Skin and Hair Care*, Idid, p. 116–119.
[10] *A.M.A. Book of Skin and Hair Care*, pp. 118–119.
[11] Department of Health and Human Services, Public Health Service, National Institute of Environmental Health Sciences, National Toxicology Program reported in the Federal Register: Apr. 21, 1997 (Vol. 62, Number 76), pp. 19348–19349 (Notices). As of this date, the DHHS has solicited comments regarding chemicals sodium thioglycolate (CAS367-51-1) for reproductive toxicity (noting high production and occupational and human exposure in hair care products).

Bisulfite wave creams and straighteners also produce reversible bond changes. Bisulfite is milder on skin and the chance of hair damage is lower, permitting these products for home use. In the straightening procedure, bisulfite lotion is applied to clean, damp hair which is then covered in a plastic turban for about 15 minutes. The hair is then combed for 15 to 20 minutes to produce the degree of straightness desired. The disulfide bonds are relinked into a new orientation by rinsing the hair with water and applying an alkaline stabilizer solution followed by a conditioner. Results from this method are similar to alkali straighteners and superior to thioglycolates.

Like other known methods, alkali lotions cannot be used on irritated or injured scalps. As new hair grows in, it alone should be exposed to the chemical straighteners, an often delicate and difficult procedure that avoids lotion contact with both the scalp and the previously treated hair. In this method sodium hydroxide lotion is applied to the hair and smoothed flat with finger pressure. A 'normalizer' pre-shampoo rinse is then applied followed by a water rinse. The hair is then shampooed twice, conditioned and administered a setting/styling/wrapping lotion prior to styling and drying. Some brands also add a leave-in "perm strengthener" after shampooing.

The "no lye" method uses lithium hydroxide, also a human toxin, in combination with other ingredients as the relaxing agent. This method begins with a moisturization additive, followed by the lithium cream, a pre-shampoo normalizer, neutralizing shampoo and a revitalizing conditioner. The user is also cautioned against skin and scalp burns, possible hair loss and eye injury. The product is contraindicated for persons with damaged or chemically-treated hair and irritated scalp.

Acetamide ($CH_3CONH_2$) is an organic, crystal compound in the urea and guanine series which has recently been formulated into a cosmetic spray-on, straightener styling aid for use between shampoos. Damp, clean hair is sprayed with the acetamide aerosol and blown dry with tension brushing. Acetamide is a known irritant to the eyes, nose, and throat and has shown low-to-moderate acute toxicity from oral exposure, including liver tumors, in animal studies (Group 2B, possible carcinogen, IARC classification).

Other methods of breaking disulfide bonds in hair employ high-heat appliances. In this method heat combs set at 300° F. are pulled quickly through long hair, which instantly breaks disulfide bonds leaving the hair straight. This process can result in damaging hair permanently if the temperature and combing speed are not carefully managed.[12]

[12] Significant alteration occurs to hair at 140° to 250° F. Large-scale irreversible damage occurs above 300° F. *American Medical Association Book of Skin and Hair Care.*, p. 193.

U.S. Pat. No. 3,654,936 to Wajaroff describes the use of a keratin softener for straightening hair. In this method hair is treated with a reducing agent then straightened by the action of a "keratin softener" combined with swelling or penetration-promoting agents, while being straightened mechanically prior to the application of a fixation agent.

Other straightening methods include the use of humectants such as fatty acid lactylates and fatty acid glycolates to improve the hair's texture,[13] and the use of dipropylene glycol monomethyl ether as a swelling and penetrating agent.[14]

[13] U.S. Pat. No. 4,424,820, "Hair Straightening Compositions Containing Fatty Acid Lactylates and Glycolates and their Method of Use", Cannell, D. et al., assigned to Redken Laboratories.
[14] U.S. Pat. No. 4,859,459, "Method of Shaping Human Hair Using Dipropylene Glycol Monomethyl Ether", Greiche, J., et al., assigned to Wella Aktiengesellschaft, Germany.

Nail Hoof, and Hyperkeratosis Treatment

Mammalian nails and hooves and hyperkeratotic skin tissues such as callouses, corns and the surrounding mounds of warts are also high in keratin protein and can be denatured by the compositions of the invention. This denaturing of keratin leads to the softening of surface keratin and keratin debris, the buildup of nail tissue under the nail plate medically known as onychomycosis (OM), a localized infection of the nail or nail bed caused by pathogenic fungi. While prevalent in both finger and toe nails, it is primarily a disorder of the toenails occurring more often in older adults and constituting between 18% and 40% of all nail disorders. Also known as tinea unguium, OM is caused by microorganisms of the dermatophyte family, *candida albicans* and, rarely, the mold *scopulariopsis brevicaulis*. OM initially presents as a thickening and opacification of the nail plate edges. White patches may form where air pockets occur and various degrees of erosion, subungual hemorrhaging and other discoloration can result as the fungus advances. Total dystrophic OM, which is the most advanced and common form, causes the nail plate to become thickened with underlying keratin debris elevating the nail plate at a severe angle to the nail bed. Pain and difficulty in wearing foot apparel is often experienced.

Current Methods of Treatment

Because dermatophytes are invasive to the keratin nail tissue, nail fungal infections are one of the hardest forms of external infection to treat. While current treatments are somewhat effective, they have adverse side-effects, and are contra-indicated for patients taking certain drugs. Recently FDA-approved Terbinafine (Lamisil®) is now the generally-accepted drug of choice. It is a synthetic allylamine compound that inhibits the action of squalene expoxidase, a crucial enzyme in the formation of ergosterol, leading to membrane disruption and dermatophytic cell death. Oral terbinafine is generally well-tolerated with the most common adverse effects being nausea, abdominal pain and allergic skin reactions. Taste disturbance and hepatic toxicity have also been reported. Itraconzole (Sporanox®) is an alternative treatment which inhibits cytochrome P450 dependent synthesis of ergosterol. Reported side effects include headache, rhinitis, upper respiratory tract infection, sinusitis, reversible hepatitis, severe hepatotoxicity, diarrhea, dyspepsia, flatulence, dizziness, nausea, cystitis, urinary tract infection, myalgia, appetite increase, constipation, gastritis, gastroenteritis, myalgia, fever, pain, tremor, herpes zoster, asthenia, pharyngitis, rash and vomiting. Numerous drug interactions with itraconzole also cause plasma level increases and decreases. Clinical trials indicate that 89% of users noted improvement, 14% were cured and 21% of the cured group experienced reinfection. In the past, griseofilvin, an antifungal agent derived from a number of penicillium species inhibiting cell division and nucleic acid synthesis, ketoconazole, an oral or topical synthetic ioxolane imidazole compound which interferes with the biosynthesis of ergosterol, and fluconazol, an oral synthetic bis-triazole compound that inhibits the cytochrome P450-dependent 14 alpha-demethylation step in the formation of ergosterol, were prescribed for OM and, for some patients, remain the drug of choice, despite a higher risk of severe side effects.

Like oral methods, topical medications for OM require continuing treatment over many (i.e., 3–18) months. Removal of the nail by surgical means or by 40% urea cream may hasten the total duration of treatment. Fungicidal creams include myconazole nitrate, clotrimazole, 10% povidine iodine and 1% econozole nitrate.

Callouses and Corns

Callouses and corns form a protective thick pad on the stratum corneum layer of the skin in response to repeated irritation or rubbing. They can appear anywhere on the body but are generally found over a bony spot on the hands, feet and elbows. A corn is a thickened area of keratin that occurs on the feet, usually over the joints of the toes. Corns can become painful if the thickened skin transfers pressure to the underlying bone. Callouses and corns can be treated with salicylic acid, pumice stone or by excision.

Plantar Warts

Plantar warts are hyperkeratotic lesions usually on the plantar surface (sole of foot) or palms caused by the Human Papilloma Virus (HPV) which attacks the epidermal layers through direct contact. The glabrous skin of soles and palms can be preferentially involved in various disorders of keratinization due to the higher concentration of keratin at these sites. Failure to treat plantar warts can lead to their transmission, recurrences and pain. Although self-resolving, they can be treated by cryotherapy, surgically (curettage, electrodesiccation), with topical acids (salicylic acid, lactic acid or cathandrin) or immunologically. Keratin is also found in abnormally high concentration in the non-ridged skin of patients with the Dowling-Meara form of epidermolysis bullosa simplex, for which the invention is also a treatment. While the invention cannot disable the virus, it can reduce the size of the surrounding keratinous tissue which is the source of plantar wart pain.

Psoriasis and Ichthyosiform Dermatoses

Psoriasis is an inherited disorder of keratin formation in which control of normal epidermal cell turnover has been lost leading to the production of abnormal keratin scales and raised formations known as plaques. The turnover rate of psoriatic keratinocytes (from basal layers to stratum corneum shedding) is only 3–4 days as compared to the 26–28 normal cell cycle. Psoriasis is characterized by scaling papules, most often occurring on the elbows, knees, hands, feet and scalp. Lesions appear pinkish in color with silver-white scales, are sometimes pruritic, and can be debilitating psychologically. Acitretin (retinoid-Vitamin A-analog), calcipotriol, cyclosporin and tazarotene are chemicals used to treat psoriasis by modulating the cellular differentiation of the epidermis and slowing down the production of keratin. In extreme cases, cytotoxic drugs (Methotrexate) and DNAbinding drugs (Trimethylpsoralen plus UV light) are used to slow the rate of cell division. In 30% of cases psoriasis also affects the nails and is characterized by discoloration, small pits in a thickened nail plate and onycholysis (separation of the nail late from the bed).

Hereditary ichthyosiform dermatoses are also hyperkeratotic cells which form fish scale patterns most often on the buttocks, thighs, shins, arms and backs of patients and are symptomatically treated by hydrating agents.

Acne Vulgaris and Keratosis Pilaris

Acne is a common inflammatory disease of the facial and upper torso skin in which sebaceous glands become obstructed as a result of the interplay between several factors: keratin-related chemicals, the steroid hormone, dihydrotestosterone (DHT), sebum, free fatty acids broken down from sebum, and the bacteria propionibacterium acnes. In acne the epidermal lining of the pilosebaceous duct does not keratinize properly so the keratin is not shed and instead adheres together, along with the sebum and bacteria present in the duct, causing the gland to plug and form painful, swollen, comedo lesions, commonly referred to as blackheads (open comedo), whiteheads (closed comedo) and blemishes (papules and pustules). The large, distended pore structure allows propionibacterium acnes to proliferate in combination with the chemical components of sebum resulting in the development of red pimples which, if lacerated, can leave permanent scaring. Acne is treated with Retin-A and various antibiotics to inhibit bacterial lipase production causing sebum conversion into highly irritating fatty acids.

Keratosis Pilaris is a disorder in which keratinous cells of the epidermis form plugs that fill the openings of hair follicles to form small, pointed pimples, most commonly on the upper arms, thighs and buttocks, but sometimes on the face, especially in children. The condition usually resolves in warm weather and presents only cosmetic problems.

Age Lines

Aging skin is the result of UVA and UVB light damage, and biological decline in collagen production, resulting in the slowing of cell mitosis within the dermis. Methods to reverse the appearance of fine lines and surface blemishes and stimulate skin cell renewal include beta hydroxy acids (salicylic and citric acids), Retin-A (tretinoin) and various "peeling" agents which remove the outer epidermis including the keratinous stratum corneum and attack the lower dermal layer to stimulate new collagen production. Increase collagen production has the effect of reducing age lines in the epidermis.

Background of Weak Acids

Weak acids are acids which only feebly conduct electricity (low conductivity) and are only partially ionized in solution. The conductivity of solutions of acids has been thoroughly studied and the electrical conductivity of the weak acid, glacial or acetic acid ($C_2H_3O_2H$), for example, at a molarity of 0.1 is 4.67 reciprocal ohms (mho). This contrasts to the conductivity of strong acids which ionize completely in solution and have high conductivities ranging from 60 to 350 mho at the same molarity. Weak acids ionize only partially and their ions continue to react with each other, dissociating and recombining continuously in a condition known as the position of equilibrium. As is known, this occurs because the polar water molecules start to break the acids into its ions but cannot stop them from also being attracted to each other. While water molecules are sufficiently polar to prevent any permanent recombinations of the ions of strong acids, water is less effective at this task in handling weak acids and recombination of ions begins to take place as soon as any appreciable concentration of ions is present in the solution. Once the rate of recombination catches up to the rate of dissociation both processes continue to proceed at the same rate and a state of equilibrium then exists.[15]

[15] Hess, Fred C., Revised by Thomas, Arthur L., *Chemistry Made Simple*, Rev. Ed 1984, Doubleday & Co, NY 1984, p. 71–74.

It is further known that if 0.01 mole of pure acetic acid is dissolved in a liter of water at room temperature, about 4% of the solute will be ionized by the time equilibrium is reached. However, this position of equilibrium will vary depending upon the temperature and concentration. For example, if 0.1 mol of pure acetic acid is added to a flask so that the final volume is 1 liter, only 1.3% of the acetic acid is ionized to acetates.[16] The remaining 98.7% remains in solution. The higher the percentage of weak acid, the stronger the denaturing properties of the solution by protonation of keratin's carboxylic amino acids. An increase in temperature will also shift the position of equilibrium in the direction of the process absorbing energy and make the acid more reactive with carboxylic amino acids. Thus the reactivity of the solution can be modulated by both the concentration of the solution and its temperature.

[16] *Organic Chemistry*, Ibid., p. 772.

Acetic acid ($CH_3COOH$) is a non-polar solvent (Subclass 102):

Acetic Acid Structure[17]

[17]Wade, L. G., Jr., Organic Chemistry, (Prentice Hall, 1987); See also Atkins P, Atoms, Electrons and Change, W H Freeman & Co., New York 1991, p. 46.

Acetic acid is identified as glacial acetic acid (in pure form), and in water solution as ethanoic acid, ethylic acid, methanecarboxylic acid, pyroligeneous acid, and vinegar acid.

For example, vinegar, a 5% aqueous solution of acetic acid, is produced by fermentation of sugars and starches. In fact, when fermented alcoholic beverages such as wine and cider are exposed to the air, the alcohol is converted to acetic acid.

Acetic acid is used in the manufacture of acetic anhydride, cellulose acetate, vinyl acetate monomer, acetic esters, chloroacetic acid, as well as the production of plastics, pharmaceuticals, dyes, insecticides, photographic chemicals, etc.; it is also a food additive (acidulant), a latex coagulant, oil-well acidizer and is used in textile printing.[18] Acetic acid is recognized in the art as a fixing agent of protein capable of preserving both the structure and/or chemical composition of animal or plant tissues without combining with or precipitating any proteins.[19] Acidic acid solutions for the purification of proteins include methods to purify fragments of fibrinogen important to blood-clotting.[20] It is also known in the practice of biochemistry peptide sequencing that disulfide bonds can be oxidized in vitro by the carboxylic acid, performic acid,[21] which converts all cys residues—whether linked by disulfide bridges or not—to cysteic acid residues that are stable in both acidic and basic solutions. The vulnerability of disulfide bonds to acetic acid attack has also been utilized in foodstuff processing[22] and cheese manufacture.

[18] Hawley, Gessner G., *The Condensed Chemical Dictionary*, 9th Ed., Van Nostrand Reinhold Co, New York, 1977, p. 5.
[19] Four types of fixing agents are possible: (1) Additive, coagulant, (2) additive, non-coagulant, (3) non-additive, coagulant, and (4) non-additive, non-coagulant. Other major fixing agents defined by category are: Acetone (3), chromium trioxide (1), ethanol (3), formaldehyde (2), glutaraldehyde (2), mercuric chloride (1), methanol (3), osmium tetroxide (2), picric acid (1), potassium dichromate (2) and trichloracetic acid (3).

[20] The Euglobulin Clot Lysis time test (CPT code: 85360) uses 10% acidic acid solution to precipitate fibrinogen prior to mixing it with thrombin to measure clot lysis time.

[21] Source: Biochemistry 659: Class Notes, Perdue University, 1967.

[22] Keck-Gassenmeier B., Wieser H. (1996), *Disulfide bonds in acetic acid: Soluble and insoluble glutenin fractions*. In: Gluten '96, Proceedings of the 6th International Gluten Workshop (Wrigley C. W., ed.) RACI, North Melbourne, Australia, pp. 145–148.

Previous Uses of Acetic Acid on Hair

U.S. Pat. No. 5,635,168 to Burns et al. describes a composition and a method which claims to eliminate the rinsing step between reduction and oxidation, improving feel, curl retention, color receptivity and retention, shine, and strength of the hair, and is said to prevent or repair hair damaged by chemical waving or colorants. The compositions contain, (i) a polyvalent metal compound selected from alkaline earth metals (preferably a water-soluble salt such as magnesium sulfate), zinc compounds, and aluminum compounds; (ii) low molecular weight sulfur-containing material that can form disulfide bonds involving the keratin of hair (e.g., cystine-containing materials such as polypeptide or other proteinaceous materials), and (iii) optionally, an acid, which can be a carboxylic acid (e.g., a hydroxycarboxylic acid such as citric acid) or other organic acid (e.g., acetic acid) or mineral acid, wherein the pH of the compositions is less than 10. The compositions are said to be useful for the prevention or repair of damaged hair when applied in a process involving waving (after a waving solution has been applied to the hair and before an oxidizing agent has been applied to the hair).

U.S. Pat. No. 4,030,512 to Gaetani, et al. (entitled "Hair Lacquer or Setting Lotion containing Bi- or Tri-sequenced Copolymer"), describes a hair lacquer/hair setting lotion composition in a solvent comprising 0.2 to 10% by weight of a bi- or tri-sequenced copolymer. The copolymer comprises at least one sequence of a saturated hydrocarbon chain containing 2–4 carbon atoms, or a hydrocarbon chain containing 2–4 carbon atoms and interrupted by sulfur or oxygen. In the formula of Gaetani, $R^1$ and $R^2$ are alkyl $C_{1-4}$, n is 0 or 1, and HX is hydrochloric, hydrobromic, lactic or acetic acid, and at least one sequence resulting from the anionic polymerization of a polymerizable monomer." Although acetic acid is mentioned, the composition in Gaetani is used as a temporary setting lotion that does not claim to physically alter the hair permanently. The process involves applying to the hair an effective amount of the composition, rolling the hair on rollers and applying external heat to the hair for a period of time ranging from 3 to 20 minutes.

U.S. Pat. No. 4,240,450 to Grollier, el al., describes the compositions having a combination of an anionic polymer and a cationic copolymer containing sulfonic acid, carboxylic acid or a phosphoric acid end unit, wherein the compositions are said to be useful for treating keratin materials.

Traditional and home recipes describe the use of vinegar (acetic acid) or lemon juice (citric acid) to clean hair and enhance its shine. Vinegar is recommended by the American Medical Association as an after-shampoo rinse if soap and hard water are used to clean hair. Vinegar rinse is said to remove the "scum" formed on hair shafts by the reaction of hard water minerals and salts with soap.[23]

[23] American Medical Association Book of Skin and Hair Care, Schoen, L A, Ed., J.B. Lippencott Co., New York, 1976, p. 26.

SUMMARY OF THE INVENTION

The present invention thus relates to compositions and methods for denaturing keratin tissue that permit the straightening and curling of hair, the treatment of nail fungal conditions, ingrown nails, and hyperkeratosis, particularly psoriasis, acne, callouses, corns, and warts. The invention also relates to compositions and methods for the exfoliation of the stratum corneum for anti-aging cosmetic benefit.

DETAILED DESCRIPTION OF THE INVENTION

The invention relates to compositions and methods for denaturing keratin for the purposes of safely straightening (relaxing) naturally curly and kinky hair, enhancing curl and curl retention of hair, especially in conjunction with the use of heat styling appliances, sloughing or exfoliating fungus-infected keratin of the toe and fingernail, and hyperkeratotic conditions including sloughing of psoriatic skin, plantar warts, and exfoliating of corns, callouses. The invention also relates to compositions and methods for preventing and treating aging skin, as well as acne by bathing the affected or desired area in an aqueous solution containing alkanoic acid.

This is achieved by regular and periodic bathing of the keratin tissue in an aqueous solution containing alkanoic acid. The invention also relates to methods of delivering a fungicide to a patient wherein the fungicide is dissolved in an aqueous solution of at least one alkanoic acid.

As used herein, the term "alkanoic acid" refers to carboxylic acids with alkane, alkene, or similar substituents. Alkanoic acids have the following atomic grouping:

The term "weak" acid is use to refer to acids which only feebly conduct electricity (low conductivity) and are only partially ionized in solution.

The term "diluent" as used herein refers to substances used to dilute the respective acids. Suitable diluents include water and a variety of alcohols.

The preferred alkanoic acid is acetic acid ($CH_3COOH$) at 5% solution (aq) with water as the diluent. However, other alkanoic acids are suitable, including but not limited to, methanoic acid, ethanoic acid, 2-methylbutanoic acid, propanoic acid, 2-methylpropanoic acid, 2,2 dimethylpropanoic acid, decanoic acid, octanoic acid, hex-2-enoic acid, heptanoic acid, 6-methylheptanoic acid, 3-ethylpentanoic acid, 3-chloropentanoic acid, 2-hydroxypropanoic acid, 2-chloro-4-hydroxyhexanoic acid, hexanedioic acid, octadecanoic acid, 4-oxopentanoic acid, and 6-hydroxy-4-oxonanoic acid.

Compositions and Method of Use. The agent for both straightening and curling hair keratin comprises a weak alkanoic acid. While the preferred acid is glacial or 5% acetic acid (aq) other weak alkanoic acids appropriate for this method include the following preferred carboxylic acids: propanoic acid, 2-methylpropanoic acid, 2,2 dimethylpropanoic acid, heptanoic acid, 2-hydroxypropanoic acid, and octadecanoic acid.

Straightening of Naturally Curly or Kinky Hair. The preferred method of straightening hair utilizes a 5% solution of acetic acid in warm-to-hot tap water (90°–105° F.) at a preferred ratio of 20 parts tap water to 1 part 5% acetic acid (aq) which is freshly prepared in a basin or bowl. Kinky hair may require a higher concentration of the weak acids and concentrations may be increased to approximately 10:1 (AC:water). Effectiveness and reactivity may also be enhanced by increasing the temperature of the water.

The "position of equilibrium" of the agent will vary depending upon the temperature and concentration. It is known that if 0.01 mole of pure acetic acid is dissolved in 1 liter of water at room temperature, about 4% of the solute will be ionized by the time equilibrium is reached. Less is ionized at higher concentrations making the agent a stronger straightening agent with more free ions in solution. Since an increase in temperature speeds up a process which absorbs energy and slows down one that gives off energy an increase in temperature will shift the position of equilibrium in the direction of the process absorbing energy and make the acid more reactive with the carboxylic amino acids within the keratin. Thus the preferred formulation for straightening hair is 20:1, $H_2O$:5% acetic acid (aq) with the water temperature between 95°–105° F. (40:1, $H_2O$:5% acetic acid (aq) for setting enhancement). However, the use of pure acetic acid (glacial acid), or other pure weak acid as identified above, and hot water will achieve the same results. Calculating the equivalent amount of the acids, in this case, using 20 cups or 40 cups of water to 0.4 ounces of pure acetic acid [0.05×8 oz. (1 cup of 5% acetic acid)=0.4 oz. pure acetic acid].

For hair that is difficult to straighten (such as African American hair) or hair that is very delicate or damaged (such as naturally blond and permed hair) adjustments may be made in the temperature and concentration of the method to maximize results or minimize harshness, keeping in mind that the percentage of ionization of a weak acids increases with dilution and with that ionization/dilution, a milder straightening and setting solution is formulated.

The rinse is applied by submerging clean, damp hair into a freshly-made bath of the solution for approximately 15 seconds to 60 seconds. The hair is then towel dried, optionally treated with a styling gel, and combed straight or smoothed back or around the head in a straight configuration, and air-dried or dried by heat. Once dry, the hair may be curled or smoothed by heat appliances (heat rollers, wands, blow dry brushes, heat combs, etc.) into the desired style. The rinsing procedure may be repeated daily, weekly or periodically until the desired degree of straightness is achieved. The rate of response to these treatments will depend upon the amount of curl, the porosity of the hair from previous chemical treatments, and the natural thickness of the cuticle. The more porous the cuticle the more responsive the hair to the alkanoic acid rinses. African-American hair, because it does not straighten when wet, should be pulled mechanically or assisted with heat rollers or gels after treatment.

Continuous and unmonitored immersion will eventually result in weakening and breakage of the hair shaft, as illustrated in Example 1, and continuous use should be accompanied by the addition of conditioners, hot oil/cream treatments and the trimming of dried ends, as required, to maintain shine and feel attributes. The distal ends of previously dyed, permanently waved or straightened will respond more rapidly to the alkanoic acid rinses hair, due to their increased porosity (the result of more frequent exposure to chemicals and the sun, etc.) and may require trimming or extra conditioning.

Improved Heat-Set Curl Retention and Protection from Humidity

This invention also encompasses compositions and methods for safely improving the retention of hair styles formed by the use of appliances, particularly heat appliances, by bathing hair in a freshly-prepared mixture of acetic acid ($CH_3COOH$) at 5% solution (aq) and water. Human hair treated with one or more aqueous-alkanoic acid rinses will retain its styling longer, especially when styled by heat appliances (blow-dryers, heat curlers, heat wands, heat combs/brushes) and, with the loss of hydrogen bonding, become desensitized to high humidity.

The preferred method comprises the use of a shampoo and rinse-off conditioner, followed by submersion of damp, clean hair into a warm to hot (90°–105° F.) solution at a preferred ratio of 40 parts tap water to 1 part 5% acetic acid (aq) which is freshly prepared in a basin or bowl. The use of pure acetic acid (glacial acid), or other pure weak acid as identified above, and hot water will achieve the same results. Calculating the equivalent amount of the acids, in this case, using approximately 40 cups of water to 0.4 ounces of pure acetic acid [0.05×8 oz (1 cup of 5% acetic acid)=0.4 oz. pure acetic acid]. The rinse is applied by submerging clean, damp hair in the bath of the solution for approximately 15 to 30 seconds. The hair is then towel dried, optionally treated with a styling gel, and styled as usual. Subsequent room temperature or heat-set curls will be tighter, longer lasting and desensitized to high humidity. Appropriate conditioners, hot oil/creams and moisturizing products should be applied if the hair is frequently treated or has been chemically or sun damaged to maintain moisture levels and feel attributes.

Softening of Nail Tissue

The methods and compositions described herein gradually soften, dissolve and permit excoriation of the surface and excess nail tissue known as keratin debris, in which fungi survive. By attacking certain amino acids of the affected keratin debris, it becomes softened, permitting its safe and painless removal, gradually and over time, while adjacent healthy tissue which contains less keratin is left unaffected by the treatment.

Acidic and propionic (propanoic) acids are known to have antifungal properties, particularly against pseudomonas *aeruginosa, candida* and *aspergillus* strains. The use of these acids for the treatment of nail fungal diseases, however, has not been effective as these acids cannot be safely applied to nail tissue at high strengths, and cannot penetrate to the source of the fungus which lies subungually below the nail and within the hard keratin debris.

It should be noted that while the presence of an alkanoic acid in a low concentrate aqueous solution may enhance the antifungal results of the method in treating OM, this invention treats keratin, the habitat of the fungus. By eradicating that habitat, as a sloughing agent, the fungus itself is eliminated. This is similar to the current research exploring anti-angiogenic agents which prevent cancer tumors from sustaining a vascular system. By selectively eliminating the tumor's environment, it dies. Similarly, OM is treated by dissolving the specific keratin tissue in which OM fungi survive.

Additionally, when the method of treatment disclosed herein is followed, the known anti-fungal properties of acetic and propanoic acids are effectively delivered to the nail fungal habitat allowing them to come into contact with the fungal strains and act as fungicides. This is achieved by the electrostatic action triggered by the inability of alkanoic acids to ionize in water and protonate the carboxylic amino acids of keratin protein. The invention is thus a safe and effective, non-systemic treatment of nail fungal conditions by a novel method of delivery of a known fungicide, and denaturing of keratin, as well as a safe and effective treatment of generalized callouses, corns and skin mounds created by warts which dissolve and slough as a consequence of the protonation of the two carboxylic amino acids in keratin, glutamic acid and aspartic acid which, in turn, leads to the denaturing of cystine and the resultant cleavage of disulfide bonds. It is this pathway of events which results in the physical manifestation of softened keratin tissues. Once softened after several weeks of soaking treatments, high keratin-containing tissue can be safely lifted from normal tissue by dissolving, scrapping, excoriation or, in the case of skin tissue, peeling. In OM, fungus is no longer present as a consequence of the removal or sloughing of its environment.

The methods and compositions described herein gradually soften, dissolve and permit excoriation of the excess nail tissue in which the fungi collect and survive. By attacking the keratin debris of the nail and permitting its safe and painless removal, gradually and over time, the remaining tissues—healthy nail and normal, or soft skin—containing lower levels of keratin, are left unaffected by the treatment and, in the case of OM, fungus-free. The method and compositions described herein exposes the nails to a one to three month regimen of twice daily foot baths in which an alkanoic acid is dissolved in warm water at a preferred ratio of one part acid to 16 parts warm water. The electrostatic action of the weak acid in water (causing protonation of glutamic acid and aspartic acid within keratin protein and the cleavage of its disulfide bonds) gradually softens the keratin of the nail. Keratin debris softens at a greater rate than the healthy nail plate, resulting in its dissolution and easy removal by mechanical means. Discoloring fungus on the surface and edges of the nail plate is also dissolved along with surface nail plate cells, leaving the nail clear and topically fungus free. Simultaneously, the non-ionized alkanoic acid electrostatically attacks the carboxylic amino acids within subungual keratin debris softening it until eventually the base, lumina area, is exposed and debris dissolved from this area as well. As the keratin debris softens the treatment can be hastened by gently boring into the keratin debris with a small nail cuticle tool or pick and creating irrigation channels through which the acid bath solution can penetrate to further speed the softening process. Without an environment in which to survive, the fungus itself disappears. The process takes from one to three months depending on the amount of existing debris material to be dissolved, softened and excoriated (see Example 9 and FIG. 10).

A similar procedure and composition can be used for a hand bath in which fingernails contaminated with fungal infection can be treated.

Softening of Ingrown Nail Tissue

Ingrown nails result when a deformed fingernail or toenail grows improperly into the skin or when the skin around the nail grows abnormally fast and engulfs part of the nail.[24] A series of treatments for ingrown nails, particularly ingrown toenails can be beneficial when the edges of the nail have grown into the surrounding skin and removal by cutting is difficult and painful. Baths in a 20:1 (alkanoic acid:water) solution of the agent will soften the keratin within both the nail and irritated, hardened skin by the mechanism described. Once softened, the nail can be lifted with less pain and trimmed appropriately.

[24] *The Merck Manual of Medical Information* (Home Edition), Berkow, R., Ed., Merck Research Laboratories, Whitehouse Station, N.J., 1997, p. 260.

Softening of Callouses Corns and Warts

The method and composition of this invention can be used to treat hyperkeratosis and soften callouses, corns and the hardened skin around warts which may be difficult to treat by the currently proscribed methods either because of their large size (in the case of generalized foot callouses), or the difficulty in confining the strong acids of conventional corn medications to the localized corn tissue. Callouses and corns, as well as the tissue which builds up around warts, such as plantar warts, contains higher amounts of keratin than normal skin. Thus the aqueous alkanoic bath formulations can be used as a soaking therapy and function as a sloughing agent for the removal of this unwanted skin tissue. The treatment regimen calls for twice-daily baths in an aqueous solution of warm water freshly mixed at the preferred ratio of 1 part alkanoic acid to 16 parts water. Depending on the patient's condition, the outer layers of the callous, corn or wart will begin to soften and then peel away leaving fresh pink skin at the completion of treatment. As normal skin does not contain high levels of keratin, there is no damage to normal skin during the treatment. The use of a sanding board on dry callous areas before each treatment will hasten the process of exfoliation. Patients can reduce treatment to once daily and then once weekly to prevent recurrence. (See Example 9).

It should be noted that the elimination of the toughened mounds around plantar's warts which the human body uses as a defense against the invading plantar virus, is what makes plantar warts so painful to walk on.

Treatment of Psoriasis

Psoriatic lesions should be soaked in a warm aqueous solution of alkanoic acid, the preferential acid being acetic acid (5%) at a ratio of 16 parts water to one part acid (½ cup to 2 quarts water) twice daily for 5 to 10 minutes.

Treatment of Acne

If the acne is located on the back or upper shoulders the patient can lie in a warm bath of aqueous solution of alkanoic acid, the preferential acid being acetic acid (5%) at a ratio of 16 parts water to one part acid (½ gallon to 8 gallons water) for 10 minutes twice daily. Acne of the face can be treated by placing the face (with eyes tightly closed) in a bowl of warm water to which a 16 to 1 ratio of alkanoic (preferably 5% acetic acid at ½ cup acid to 8 cups warm water) for 30 seconds to a total of 2 minutes twice daily, depending upon the severity of the condition.

Treatment of Age Lines

Removal of keratin from the epidermis can be accelerated by monthly bathing of the face (with eyes tightly closed) in a solution of warm water to which a 16 to 1 ratio of alkanoic acid: $H_2O$ (preferably 5% acetic acid at ½ cup acid to 8 cups warm water) for 30 seconds, followed by towel drying and the application of a heavy cream or oil, preferably containing vitamin E.

Mechanism of Action. While not wishing to be bound by any one theory, it is believed that the present compositions are capable of gradually and by repeated applications altering the secondary structure of keratin's polypeptide chain by reacting with the carboxylic acids and in turn the amine bases of this protein, such that glutamic acid and aspartic acid are protonated with their electron charge changing from negative to neutral/positive. This reaction is believed to result in the following denaturing events:

1. Protonation of glutamic acid and aspartic acid is known to cause these amino acids to turn inward on themselves or "inside out", changing at these locations the hydrogen bonding distances and strength.

2. Salt bridges are also cleaved with the change is aspartic and glutamic acid electron charge. As is known, these negatively-charged amino acids form ionic bonds, also know as salt-bridges, with arginine and lysine which are positively charged. When the former lose their charge the ionic bonds cleave and the keratin is further denatured.

3. Disulfide bonds "let go", it is thought, as protonation deconfigures the protein's secondary structure. These bonds are still in place but no longer anchored on the chain.

Once a percentage of the ionic, hydrogen and cysteine bonds are cleaved by repeated rinsing with the weak alkanoic acid solutions, naturally-curly hair will remain straight with improved response to heat curling and reduced response to humidity. Likewise, straight hair treated by this method will retain heat-induced curls more intensely and longer and will resist the loss of curl because of humidity (hydrogen bonding). Likewise, keratin in nail tissues and hardened skin will soften and eventually slough.

It will be appreciated that the compositions may be altered to mask the scent of the acid and can be administered in conjunction with other compositions and methods of treating and styling hair such as hair sprays, shampoos, conditioners, hot oil treatments, styling gels, heat curling, heat combing, chemical processing (e.g., dyeing, bleaching, alternative methods of chemical straightening and permanent waving, etc.). The compositions may be used in combination with hair conditioners such as hydrolyzed soy protein, safflower oil, aloe vera and other natural or synthetic moisturizers, glycerin, lactamide MEA, panthenol (Vitamin B), keratin amino acids, phytolipids, Shea butter or lanolin, mineral oil, petrolatum, laneth-15, PEG40 Stearate, milk protein, methylparaben, papaya and other fruit extracts, chamomile, anti-oxidants such as vitamin E, gamma linolenic acid, babassu oil, evening primrose oil, lesquerella oil, jojoba oil, rose hips oil and other plant oils, sea kelp; sunscreen factors; styling gels and aerosols, witch hazel and other natural or synthetic setting agents; salicylic acid, quaternium 15, thymol, eucalyptol, methyl salicylate and other anti microbial agents, coal tar solutions, and other compounds medicinal or cosmetic to hair and scalp; perfuming masks such as menthol, floral and other fragrances, caramel, artificial colorants, and other enhancers.

The following examples will serve to further typify the nature of the invention, but should not be construed as a limitation on the scope thereof, which is defined solely by the appended claims.

The method of hair straightening and curling by the preferred weak acid, a 5% solution of acetic acid combined with water, was demonstrated in several assays using subjects with a variety of hair types.

In a preferred embodiment, the invention relates to compositions for the treatment of nail fungal conditions comprising at least one alkanoic acid in aqueous solution, wherein the ratio of said alkanoic acid to water is between about 1:16 and about 1:20, and the concentration of said alkanoic acid is between about 1% to about 20%.

In another preferred embodiment, the invention relates to compositions for the treatment of at least one of corns, callouses, hardened keratinous tissue of warts, and Dowling-Meara form of epidermolysis bullosa simplex comprising at least one alkanoic acid in aqueous solution.

The invention further relates to compositions for the treatment of hyperkeratosis including psoriasis and ichthyosiform dermatoses, comprising at least one alkanoic acid in aqueous solution.

In yet another preferred embodiment, the invention relates to compositions for the treatment of at least one of acne and keratosis pilaris comprising at least one alkanoic acid in aqueous solution.

In still another preferred embodiment, the invention relates to compositions for the treatment of age lines comprising at least one alkanoic acid in aqueous solution.

The invention further relates to methods of treating at least one of psoriasis and ichthyosiform dermatoses comprising soaking an affected area in an effective amount of at least one alkanoic acid in aqueous solution. The invention also relates to methods of treating nail fungal conditions comprising soaking an effected area in an effective amount of at least one alkanoic acid in aqueous solution. The invention also relates to methods of treating at least one of acne vulgaris and keratosis pilaris comprising soaking an affected area in an effective amount of at least one alkanoic acid in aqueous solution.

Additionally, the invention also relates to methods of treating at least one of surface age lines and surface blemishes comprising soaking the affected area in an effective amount of at least one alkanoic acid in aqueous solution. The invention further relates to methods of treating at least one of corns, callouses, hardened tissue of warts, and Dowling-Meara form of epidermolysis bullosa simplex comprising soaking an effected area in an effective amount of at least one alkanoic acid in aqueous solution.

The invention also relates to methods of delivering at least one of a fungicide and fungistat to a patient comprising dissolving said fungicide or fungistat in an aqueous solution of at least one alkanoic acid.

Preferred alkanoic acids include acetic acid, methanoic acid, ethanoic acid, 2-methylbutanoic acid, propanoic acid, 2-methylpropanoic acid, 2,2 dimethylpropanoic acid, decanoic acid, octanoic acid, hex-2-enoic acid, heptanoic acid, 6-methylheptanoic acid, 3-ethylpentanoic acid, 3-chloropentanoic acid, 2-hydroxypropanoic acid, 2-chloro-4-hydroxyhexanoic acid, hexanedioic acid, octadecanoic acid, 4-oxopentanoic acid, and 6-hydroxy-4-oxonanoic acid.

EXAMPLE 1

Hair Straightening Agent

Figure 1:
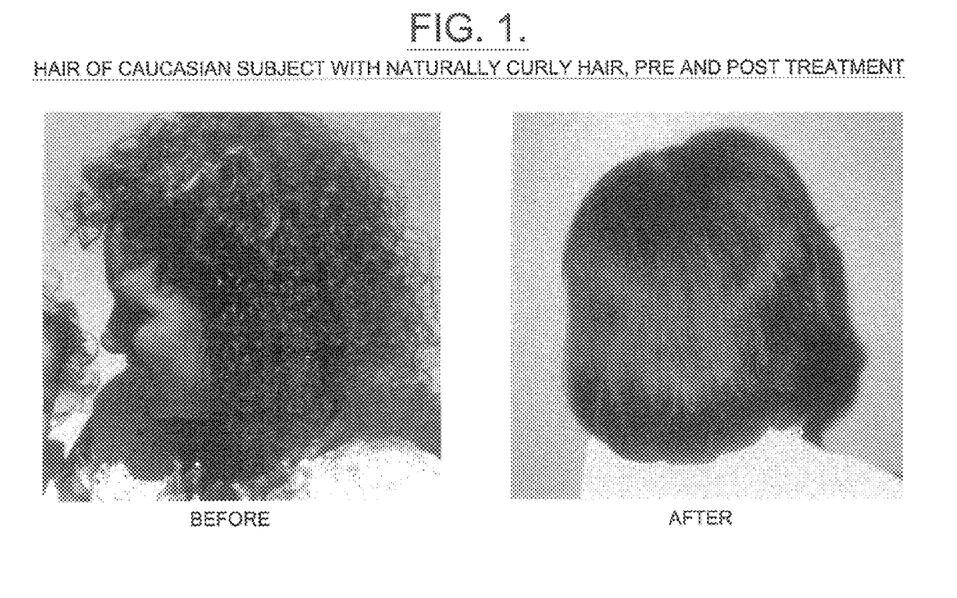
FIG. 1 (straightening) shows the hair of a Caucasian subject with naturally curly hair, pre and post treatment.

The hair of Subject A, a Caucasian female with chemically dyed (brown), naturally curly, gray hair, was bathed in a 20:1 solution of $H_2O$ to 5% acetic acid for 20 seconds and allowed to dry as a leave-on rinse bi-weekly for a period of 12 weeks for a total of 24 treatments. After 2 applications her hair demonstrated improved shine and manageability after heat setting with rollers. After 4 applications, heat curls remained in place at humidity levels of 80%. After 6 applications, her hair, formerly "frizzie" after washing, dried straight and heat-set curls remained in place at 100% humidity levels. After 8 to 10 applications, the subject reported a slight decline in shine and feel attributes and some dryness especially at the shaft ends. After 12 applications, the subject's hair was examined and compared to samples taken prior to the series of treatments. The treated shaft was visibly straighter, drier, less supple and somewhat reduced in shine. Some breakage was noted near the ends. Acetic acid baths continued at a lower AC concentration of 80:1 through week 12 and bi-weekly hot oil treatments were added. Reexamination of sample specimens during week 13 indicated that the shafts had regained moisture and shine without compromising straightness or heat curl retention. The subject discontinued acetic bath treatments after 12 weeks and indicated that no more were necessary as her hair remained easy to style and without frizziness on humid days despite frequent shampooing. The results are set forth in FIG. 1.

EXAMPLE 2

Straightening Agent

The hair of Subject B, a Caucasian male with short, dark blond, naturally curly hair, was treated with one submersion in a 20 parts $H_2O$:1 part 5% AC bath for 20 seconds. The hair was towel-dried and the rinse allowed to air dry on the hair. Observation when dry indicated that approximately 70% of the natural curl had been eliminated. The Subject did not seek re-treatment indicating he was happy with the results. He was contacted 8 weeks later and asked if his hair remained wavy rather than curly. He indicated that it was still "surprisingly manageable."

EXAMPLE 3

Hair Straightening Agent

Figure 2:
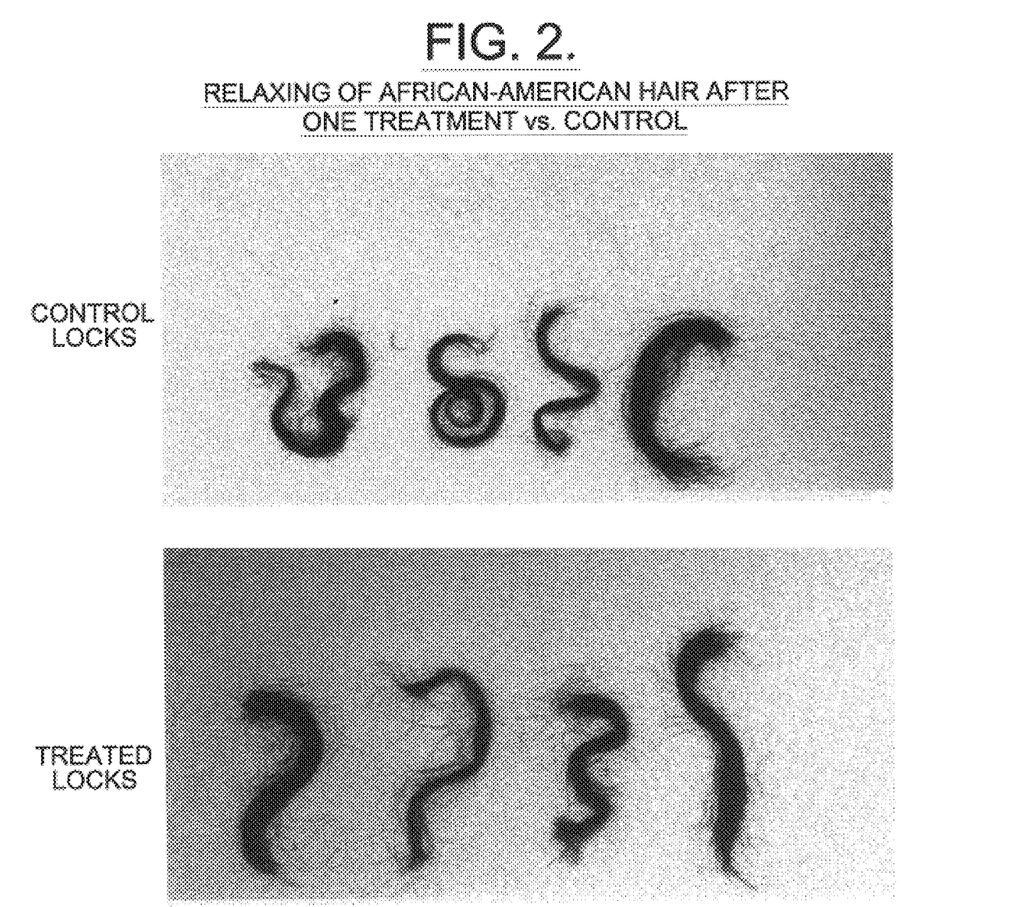
FIG. 2 (straightening) shows the relaxing of African-American hair after one treatment vs. control.

Two sets of severed locks of chemically-straightened hair (exhibiting some reversion to natural curl) from an African-American female subject were submerged for 15 seconds in a 20 $H_2O$:1 AC solution and allowed to remain on the hair for 30 minutes. A similar set of control locks were rinsed in pure tap water. Both sets of locks were then shampooed, conditioned, rinsed with water, combed out and allowed to air dry. The treated locks exhibited less reversion and curling than did the control locks. The results of this test are shown in FIG. 2: Relaxing of Previously-Straightened African-American Hair After One Treatment vs. Control.

EXAMPLE 4

Straightening of "Virgin" African American Hair

Figure 3:
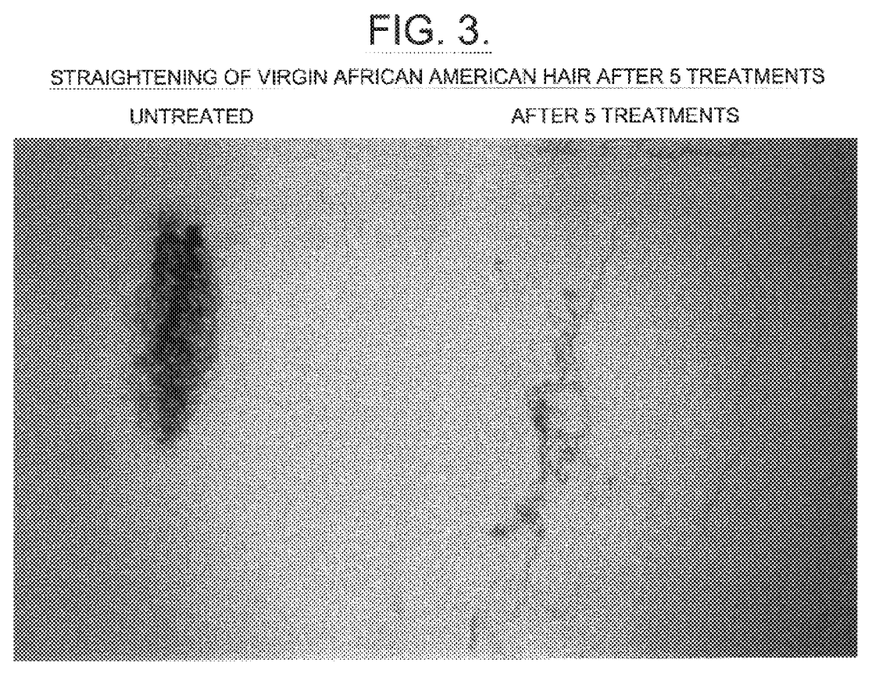
FIG. 3 (straightening) shows the straightening of virgin African-American hair after 5 treatments.

A lock of hair from a middle-aged African American woman which had never been treated with permanent waving or straightening chemicals or dyes was given five treatments at a concentration of 20:1 (AC:$H_2O$) and compared to the untreated control. Since African American hair does not straighten of its own accord when submerged in water the method requires some mechanical assistance as the hair is dried. This was done with a thick styling gel (4th treatment) and with scotch tape (5th treatment) after the hair had begun to lose its curl on its own (1st–3rd treatments). In practice, the hair may be pull straight while drying or affixed with styling gels. The results of this test are shown in FIG. 3.

EXAMPLE 5

Curl Retention Agent of Chemically Straightened Hair

Figure 6:
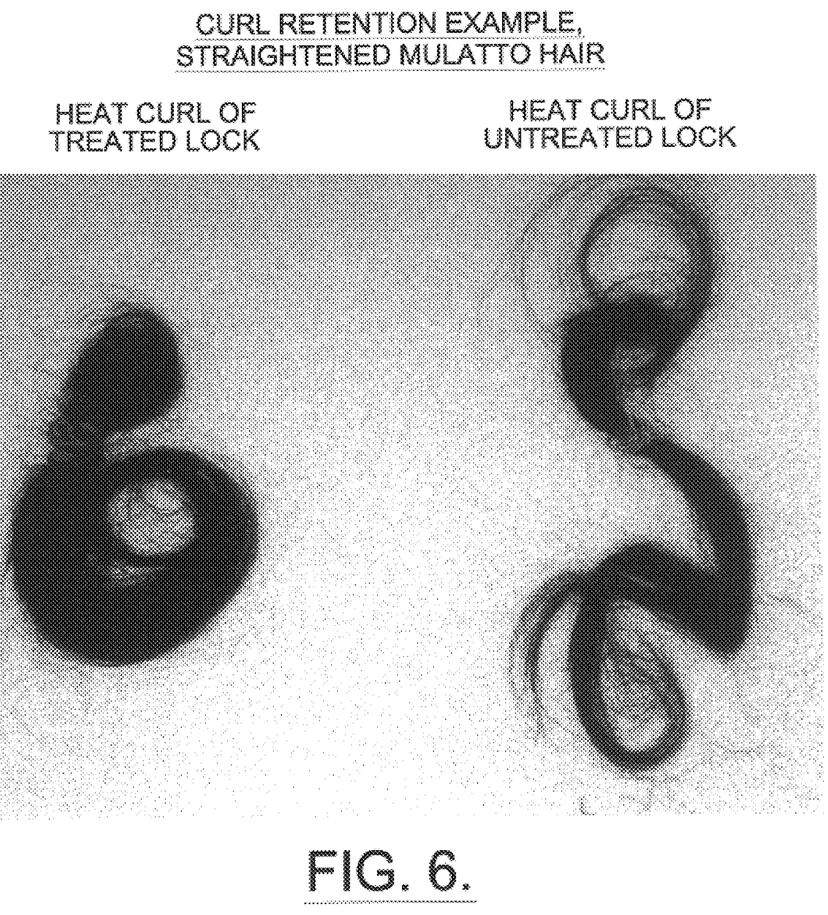
FIG. 6 (curling) shows curl retention of straightened mulatto hair.

A severed lock of the hair of a middle-aged, South-American woman of mulatto origin whose dark-brown hair had been previously straightened was treated by 15-second immersion in 40:1 solution, air-dried and heat set. An untreated control lock was submerged in pure tap water and similarly processed. Both locks were then compared for curl retention: the treated lock retained the shape of the roller curler, while the water-treated lock fell loosely in a helical shape in a 4-inch spiral. The results are set forth in FIG. 6: Curl Retention Example, Straightened Mulatto Hair.

EXAMPLE 6

Hair Curling Agent

Figure 4:
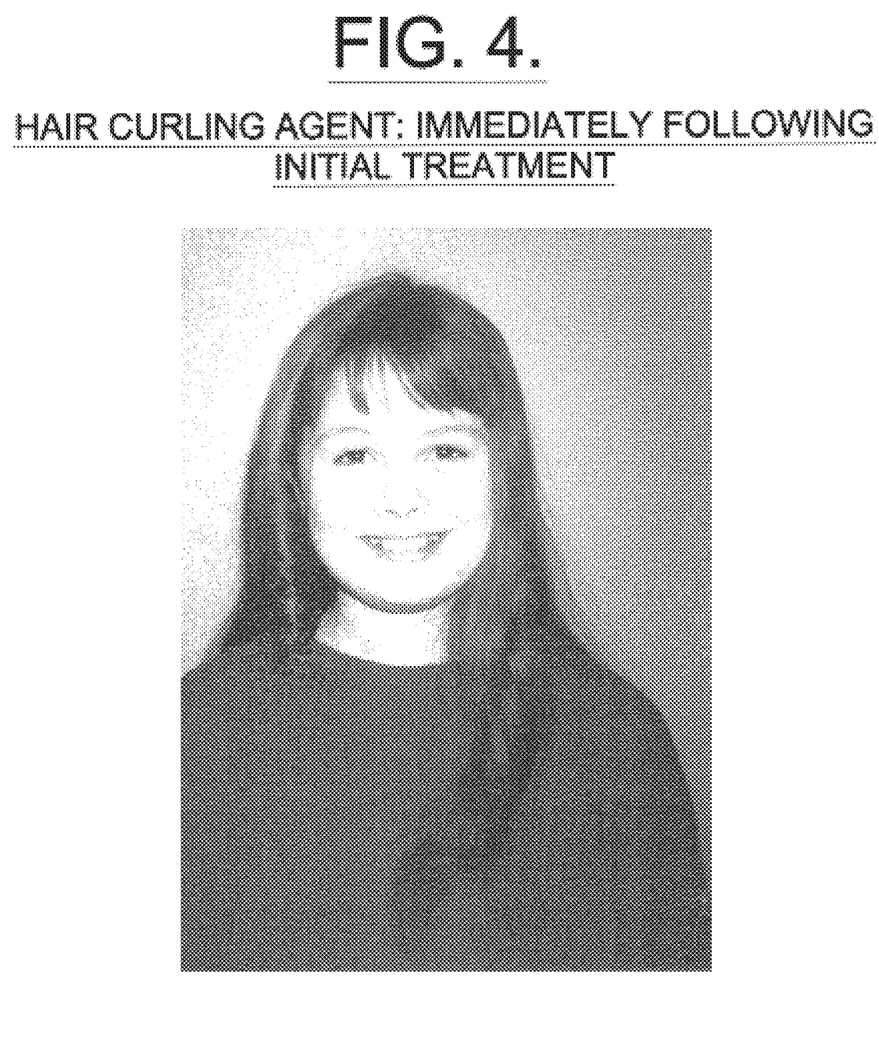
FIG. 4 (curling) shows the results of the hair curling agent immediately following initial treatment. The left side of the photo represents the treated and curled portion, and the right side of the photo shows the untreated, uncurled natural hair.

The medium brown, modestly-wavy, long hair of a young (11 years) Caucasian female was the subject of a side-by-side curl retention comparison. A 10-inch lock of hair was treated for 15 seconds with a the warm 40 $H_2O$:1 AC solution, while a second lock of equal length was treated with warm, untreated tap water. After towel drying, both sides were rolled in heat curlers and allowed to dry for 5 minutes. The treated swatch resulted in a tight curl that extended 3 inches from the point of styling. The untreated lock exhibited in a curl extending 7 inches. See FIG. 4: Hair Setting Agent: Immediately Following Initial Treatment.

Figure 5:
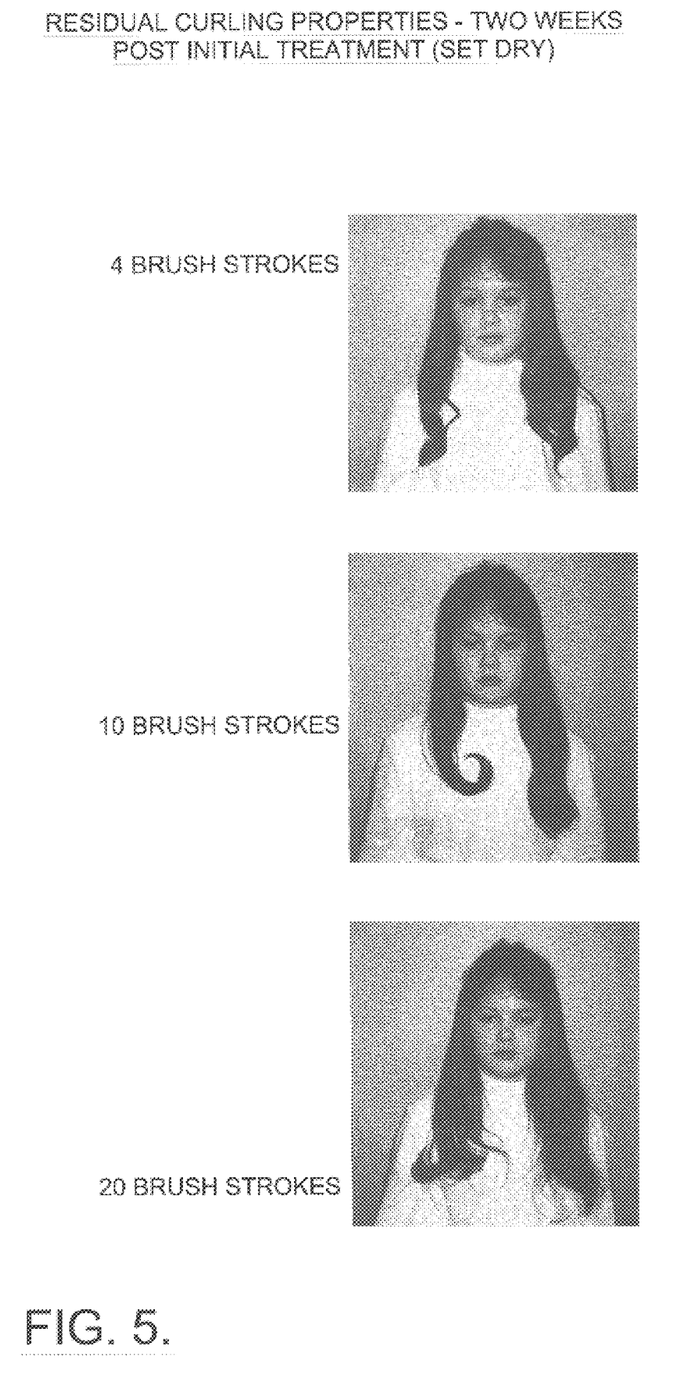
FIG. 5 (curling) shows residual curling properties of the formula two weeks after initial treatment with both side being dry set, and brushed out at 4 brush strokes, 10 brush strokes, and 20 brush strokes, respectively.

After three shampoos and the passage of 14 days, the same locks were heat styled (dry) in a similar fashion without further treatment. The elasticity of the two locks were again compared. After 2.5 minutes of heat application the treated curl was 50% shorter (tighter) than the untreated lock. Both locks were then brushed 4, 10, and then 20 times. Between brushings the length of each lock was measured and photographed. After each brushing series the treated lock retained its curl in a tighter conformation than the untreated lock averaging about one-half the elasticity (See FIG. 5).

EXAMPLE 7

Curl Retention of Occidental (Asian) Hair

Figure 7:
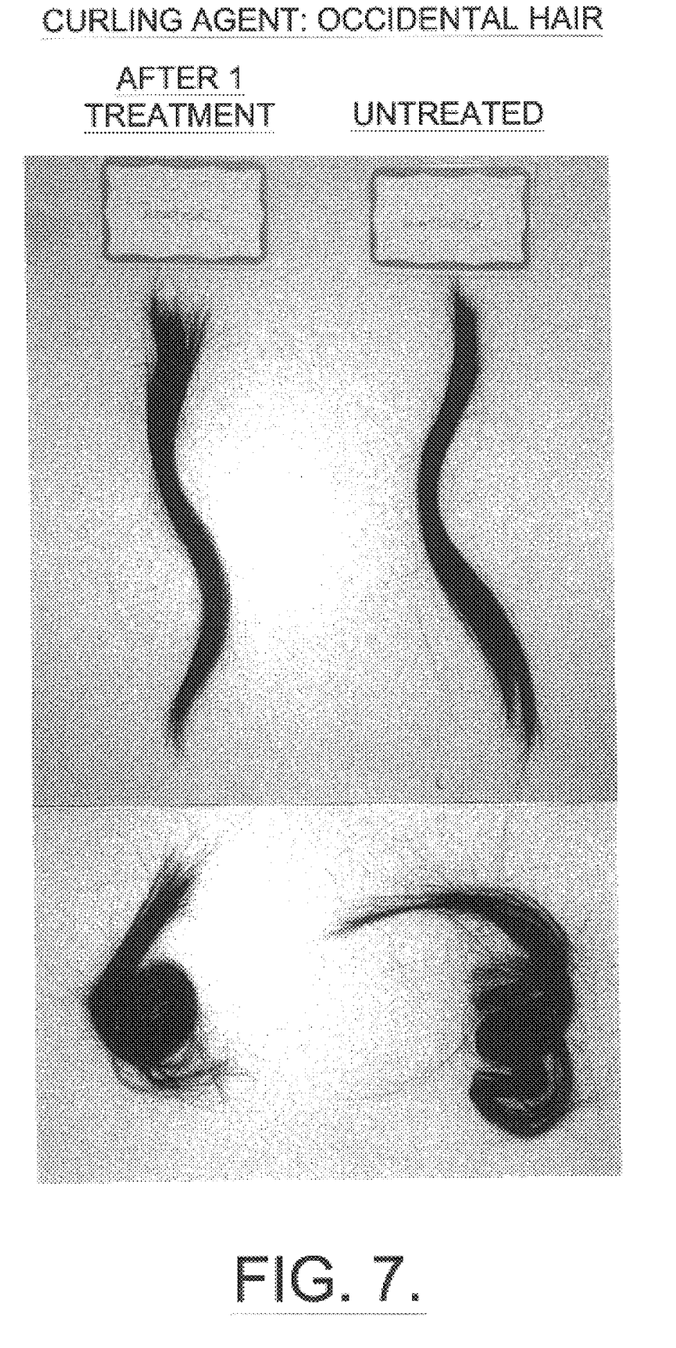
FIG. 7 (curling) shows the curling abilities of the formula on Occidental Hair.

The locks of hair from an Occidental woman of middle age were treated with one rinse of 40:1 (AC:$H_2O$) for 30 seconds, as was a control lock submerged in plain water for a similar period. Both locks were allowed to dry and heat-set with one roller. After 5 minutes the rollers were removed. The results of this test are in FIG. 7.

EXAMPLE 8

Softening of Nail Tissue

This subject experienced considerable softening and malleability of her fingernails while treating hair, reflecting the high percentage of keratin in fingernails. Her fingernails became "bendable" and unable to retain length as a result of repeated immersion in the AC:water solutions.

EXAMPLE 9

Treatment of Onychomycosis and Hyperkeratosis

Figure 8:
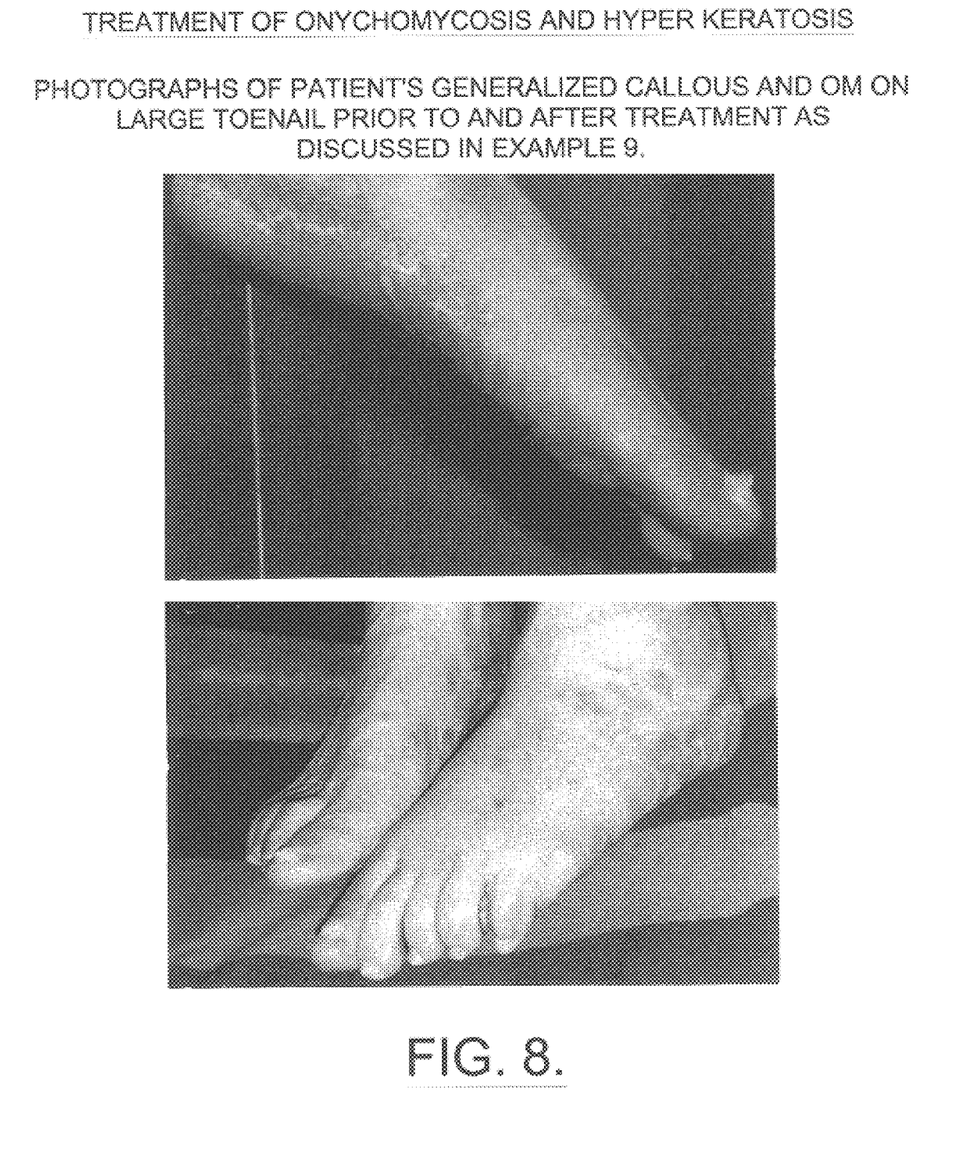
FIG. 8 shows the results of treatment of onychomycosis and hyperkeratosis. The photographs show the patient's generalized callous and OM on large toenail prior to and after treatment as discussed in Example 9. This example also shows hyperkeratosis and callouses (pre and post-treatment) in the patient.

A 76 year old male patient who reported suffering from onychomycosis on all toe nails for 30 years as well as generalized foot callouses was selected for treatment. Both large toe nails had lifted at a 45° angle off the nail bed, being compacted subungually with keratin debris. The patient also suffered from a generalized callous along the outer lateral edges of the soles of each foot. He was placed on a twice daily, 5 minute soak, foot bath regimen for eight weeks. After two weeks, the keratin debris had softened on the outer edges and could be irrigated by boring with a fine instrument to permit greater exposure to the weak acid bath solution. After four weeks the yellow color of the nail surfaces had resolved to clear and the patient's large toe nails began to flatten as keratin debris continued to slough. At the end of six weeks, much of the fungus had disappeared in tandem with the loss of keratin debris and the callouses had pealed off revealing soft skin beneath. The small toe nails appeared completely rejuvenated. At eight weeks, the patient's toe nails were free of both keratin debris and the fungus they harbored and new nail growth was adhering to the nail bed (see FIG. 8).

EXAMPLE 10

Treatment of Ingrown Nails

Ingrown toenails and fingernails are treated in the following manner. An aqueous bath solution is prepared by mixing 20 parts water with 1 part acetic acid (5% solution). The effected nail is soaked in the solution for 1–5 minutes, depending upon severity, twice daily until it can be comfortably extracted from the embedded area and trimmed.

EXAMPLE 11

Prevention of Ingrown Nails

Treatment or prevention of ingrown toenails and fingernails is effected in the following manner. An aqueous bath solution is prepared by mixing 40 parts water with 1 part acetic acid (5% solution). The effected nail is soaked in the solution for 1–5 minutes, depending upon proclivity of the patient to ingrown nails, once or twice weekly.

EXAMPLE 12

Treatment of Psoriasis

An elderly man who reported suffering from patches of psoriasis for many years on his arm, neck and head, soaked his arm in a 5% alkanoic aqueous solution at 1:16 concentration for ten minutes twice daily. After just two treatments he observed the clearing up of little bumps and scales and a smoother "feel" to the skin. This treatment can also be used in combination with topical psoriasis creams, gels or solutions such as Lidex. Ichthyosiform dermatoses is treated in a manner identical to the treatment for psoriasis described above.

EXAMPLE 13

Treatment of Acne Vulgaris

A preteen female presented with small, emerging, red pimples on both cheeks. With closed eyes, she submerged her face in a warm aqueous solution of 5% acetic acid diluted with water at 1:20 for 30 seconds. The following day, the redness and elevation were resolved. In more serious cases, especially of late-teen, male acne, the treatment may incorporate soaking the affected areas a stronger solution of 1:8 (for back and chest areas) or 1:16 (for face and neck) solutions of an 5% alkanoic acid twice daily until the pustules have faded (between 2 to 5 days) thereby avoiding the temptation to lacerate the site and risk scarring. This treatment can also be conducted in combination with topical creams and antibiotics. Keratosis pilaris is treated in a manner identical to the treatment for acne vulgaris described above.

EXAMPLE 14

Treatment of Aging Facial Lines

A woman in her early 50's who had elected not to maintain estrogen levels with hormone replacement therapy sought a method of slowing the formation of fine lines which had appeared since menopause. She was put on a regimen of once-monthly, 30-second, full-face soaks in an alkanoic-warm water solution, preferably, 5% acetic acid, at a 1:8 concentration, interspersed with a bimonthly (alternate two-week), 30-second soak of a similar solution at a milder, 1:16 concentration. Each facial soaking treatment was followed by gentle towel drying of the face and application of cold cream. Improvement in the smoothness and sheen of her skin was noted immediately. Fine lines around the eyes and mouth areas had faded within four weeks.

EXAMPLE 15

Treatment of Plantar Wart

A women in her late 20's who had been unable to rid the soles of her feet of plantar warts began a twice daily soaking regimen using the alkanoic acid (5% acetic acid) and warm water bath. The pain caused by the thick layer of callous surrounding each wart lessened and, after about a month was reduced to nominal. She continued the treatment three times weekly thereafter to prevent renewed hyperkeratosis of the plantar wart area. The Dowling-Meara form of epidemolysis bullosa simplex is treated in a manner identical to the treatment for verruca described above.

EXAMPLE 16

Method of Delivery of Antifungal Agents to Infected Nail Tissue

To a solution composed of 1:16 dilute alkanoic acid/water concentration, water-soluble fungicides such as terbinafine hydrochloride or fluconazole (slightly soluble), or fungistats, such as griseofulvincan, are added to nail fungal bath treatment as described herein. The addition of known fungal agents heightens the attack on dermatophytes or other fungal organisms within hardened nail keratin and keratin debris. As the acid/water baths continue to soften, slough and expose new keratin areas the habitating fungus are killed or rendered static by the fungicide or fungistat bath ingredient. This method of treatment may include the use of one particular alkanoic acid, acetic acid, which is a known fungicide. A topical fungicide or fungistat, such as terbinafine hydrochloride cream, myconazole nitrate, clotrimzole, 10% providine iodine and 1% econozole nitrate, may be applied between alkanoic acid/water baths and after manual excoriation of the softened nail areas to hasten the therapeutic response. This delivery or neoadjuvant treatment is also effective against ringworm and other fungal infections of the nail and hyperkeratotic skin.

What is claimed is:

1. A composition for the treatment of mammalian nail fungal conditions comprising at least one alkanoic acid in aqueous solution wherein the ratio of alkanoic acid to water is greater than about 1:20, such that the concentration of said alkanoic acid is greater than 5% by weight.

2. A composition (for the treatment of nail fungal conditions) comprising at least one alkanoic acid in aqueous solution wherein the alkanoic acid is selected from the group consisting of methanoic acid, ethanoic acid, 2-methylbutanoic acid, propanoic acid, 2-methylpropanoic acid, 2,2 dimethylpropanoic acid, decanoic acid, octanoic acid, hex-2-enoic acid, heptanoic acid, 6-methylheptanoic acid, 3-ethylpentanoic acid, 3-chloropentanoic acid, 2-hydroxypropanoic acid, 2-chloro4-hydroxyhexanoic acid, hexanedioic acid, octadecanoic acid, 4-oxopentanoic acid, and 6-hydroxy-4-oxonanoic acid.

3. A composition (for the treatment of nail fungal conditions) consisting essentially of at least one alkanoic acid in aqueous solution.

4. The composition of claim 1 in which the alkanoic acid is selected from the group consisting of methanoic acid, ethanoic acid, 2-methylbutanoic acid, propanoic acid, 2-methylpropanoic acid, 2,2 dimethylpropanoic acid, decanoic acid, octanoic acid, hex-2-enoic acid, heptanoic acid, 6-methylheptanoic acid, 3-ethylpentanoic acid, 3-chloropentanoic acid, 2-hydroxypropanoic acid, 2-chloro-4-hydroxyhexanoic acid, hexanedioic acid, octadecanoic acid, 4-oxopentanoic acid, and 6-hydroxy-4-oxonanoic acid.

5. The composition of claim 3 in which the alkanoic acid comprises acetic acid and is present in an amount of between 5% and 20% by weight of the composition.

6. The composition of claim 1 further comprising at least one of a fragrance and a colorant.

7. A method for treating a fungal condition of a mammalian nail comprising contacting said nail with a composition consisting essentially of at least one alkanoic acid and an acceptable diluent.

8. The method of claim 7 in which the alkanoic acid comprises acetic acid present in an amount of between 5 and 20% by weight of the composition.

9. The method of claim 7 in which the composition includes at least one of a fragrance or a colorant.

10. A composition for the treatment of nail fungal conditions comprising at least one alkanoic acid in aqueous solution wherein the composition does not include an antimicrobial agent.

11. A composition for the treatment of nail fungal conditions comprising at least one alkanoic acid in aqueous solution wherein the composition does not include a surfactant.

12. The composition of claim 1 wherein the ratio of alkanoic acid to water is between 8% and 20% by weight.

* * * * *